United States Patent
Brendzel et al.

(10) Patent No.: US 6,358,278 B1
(45) Date of Patent: Mar. 19, 2002

(54) HEART VALVE PROSTHESIS WITH ROTATABLE CUFF

(75) Inventors: Avrom M. Brendzel, Roseville; William R. Kramlinger, Shoreview; Michael J. Girard, Lino Lakes; Jonas A. Runquist, Minneapolis, all of MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/406,275

(22) Filed: Sep. 24, 1999

(51) Int. Cl.[7] .................................................. A61F 2/24

(52) U.S. Cl. ........................ 623/2.39; 623/2.38; 623/2.4; 623/2.41

(58) Field of Search ................................. 623/2.41, 2.4, 623/2.38, 2.39

(56) References Cited

U.S. PATENT DOCUMENTS

| | | | |
|---|---|---|---|
| 3,099,016 A | 7/1963 | Edwards | 3/1 |
| 3,143,742 A | 8/1964 | Cromie | 3/1 |
| 3,409,013 A | 11/1968 | Berry | 128/303 |
| 3,491,376 A | 1/1970 | Shiley | 3/1 |
| 3,579,642 A | 5/1971 | Heffernan et al. | 3/1 |
| 3,628,535 A | 12/1971 | Ostrowsky et al. | 128/303 |
| 3,691,567 A | 9/1972 | Cromie | 3/1 |
| 3,725,961 A | 4/1973 | Magovern et al. | 3/1 |
| 3,727,240 A | 4/1973 | Child | 29/445 |
| 3,763,548 A | 10/1973 | Anderson | 29/445 |
| 3,781,969 A | 1/1974 | Anderson | 29/445 |
| 3,800,403 A | 4/1974 | Anderson et al. | 29/445 |
| 3,825,957 A | 7/1974 | Kaster | 3/1 |
| 3,828,787 A | 8/1974 | Anderson et al. | 3/1 |
| 3,839,741 A | 10/1974 | Haller | 3/1 |
| 3,859,668 A * | 1/1975 | Anderson | 623/2.39 |
| 3,959,827 A | 6/1976 | Kaster | 3/1.5 |
| 3,996,623 A | 12/1976 | Kaster | 3/1.5 |
| 3,997,923 A | 12/1976 | Possis | 3/1.5 |
| 4,078,268 A | 3/1978 | Possis | 3/1.5 |
| 4,197,593 A | 4/1980 | Kaster et al. | 3/1 |
| 4,233,690 A | 11/1980 | Akins | 3/1.5 |

(List continued on next page.)

FOREIGN PATENT DOCUMENTS

| | | | |
|---|---|---|---|
| WO | WO 96/12452 | 5/1996 | |
| WO | WO-96/12452 | * 5/1996 | A61F/2/24 |

OTHER PUBLICATIONS

Brochure entitled: "Expanding the Inner Limits™", by St. Jude Medical, Inc. (1999).

Primary Examiner—David J. Isabella
Assistant Examiner—Urmi Chattopadhyay
(74) Attorney, Agent, or Firm—Hallie A. Finucane, Esq.; Westman, Champlin & Kelly, P.A.

(57) ABSTRACT

A prosthetic heart valve includes an orifice ring adapted to carry blood therethrough. An annular recess is formed in an outer surface of the orifice ring and has first and second axially spaced walls. A sewing cuff is adapted to be coupled to a native tissue annulus of a heart and includes an inner annular cuff portion adapted to conform to the first and second recess walls in the orifice ring. A cuff retaining ring extends around the inner annular fabric portion such that the inner annular cuff portion is positioned between the cuff retaining ring and the annular recess. The cuff retaining ring is further adapted to exert a substantially axially directed force directed against the annular cuff portion and first and second axially spaced walls of the annular recess, which is substantially greater than a radial force directed substantially inwardly by the cuff retaining ring against an annulus of the recess located between the first and second walls, whereby a controllable torque to rotate the cuff relative to the orifice ring is developed substantially due to friction between the first and second recess walls cuff portion and the annular recess.

17 Claims, 10 Drawing Sheets

U.S. PATENT DOCUMENTS

| | | | |
|---|---|---|---|
| 4,240,161 A | 12/1980 | Huffstutler, Jr. et al. | 3/1.5 |
| RE30,507 E | 2/1981 | Kaster | 3/1.5 |
| 4,276,658 A | 7/1981 | Hanson et al. | 3/1.5 |
| 4,328,592 A | 5/1982 | Klawitter | 3/1.5 |
| 4,535,483 A | 8/1985 | Klawitter et al. | 623/2 |
| 4,576,605 A | 3/1986 | Kaidash et al. | 623/2 |
| 4,599,081 A | 7/1986 | Cohen | 623/2 |
| 4,655,462 A | 4/1987 | Balsells | 277/164 |
| 4,665,906 A | 5/1987 | Jervis | 128/92 |
| 4,666,442 A | 5/1987 | Arru et al. | 623/2 |
| 4,680,031 A | 7/1987 | Alonso | 623/2 |
| 4,683,883 A | 8/1987 | Martin | 128/303 R |
| 4,705,516 A | 11/1987 | Barone et al. | 623/2 |
| 4,743,253 A | 5/1988 | Magladry | 623/2 |
| 4,790,843 A | 12/1988 | Carpentier et al. | 623/2 |
| 4,826,144 A | 5/1989 | Balsells | 267/167 |
| 4,863,460 A | 9/1989 | Magladry | 623/2 |
| 4,865,600 A | 9/1989 | Carpentier et al. | 623/2 |
| 4,876,781 A | 10/1989 | Balsells | 29/173 |
| 4,890,944 A | 1/1990 | Cousins et al. | 401/98 |
| 4,915,366 A | 4/1990 | Balsells | 267/167 |
| 4,982,727 A | 1/1991 | Sato | 128/4 |
| 5,035,709 A | 7/1991 | Wieting et al. | 623/2 |
| 5,071,431 A | 12/1991 | Sauter et al. | 623/2 |
| 5,072,070 A | 12/1991 | Balsells | 174/35 |
| 5,079,388 A | 1/1992 | Balsells | 174/35 |
| 5,104,406 A | 4/1992 | Curcio et al. | 623/2 |
| 5,108,078 A | 4/1992 | Balsells | 267/167 |
| 5,117,066 A | 5/1992 | Balsells | 174/35 |
| 5,163,955 A | 11/1992 | Love et al. | 623/2 |
| 5,178,633 A | 1/1993 | Peters | 623/2 |
| 5,197,980 A | 3/1993 | Gorshkov et al. | 623/2 |
| 5,236,450 A | 8/1993 | Scott | 623/2 |
| 5,354,330 A | 10/1994 | Hanson et al. | 623/2 |
| 5,403,305 A | 4/1995 | Sauter et al. | 606/1 |
| 5,443,502 A | 8/1995 | Caudillo et al. | 623/2 |
| 5,480,425 A | 1/1996 | Ogilive | 623/2 |
| 5,582,607 A | 12/1996 | Lackman | 606/1 |
| 5,584,879 A | 12/1996 | Reimold et al. | 623/2 |
| 5,607,470 A | 3/1997 | Milo | 623/2 |
| 5,755,783 A * | 5/1998 | Stobie et al. | 623/2.39 |
| 5,766,240 A | 6/1998 | Johnson | 623/2 |
| 5,876,436 A | 3/1999 | Vanney et al. | 623/2 |

\* cited by examiner

HEART VALVE PROSTHESIS WITH ROTATABLE CUFF

FIELD OF THE INVENTION

The present invention relates generally to heart valve prostheses. More specifically, the present invention relates to heart valve prostheses which have a sewing cuff and which have a valve body that is rotatable relative to the sewing cuff.

BACKGROUND OF THE INVENTION

Prosthetic valves are used to replace defective natural valves in human hearts. The prosthetic heart valves permit blood flow in one direction through the valve, and block blood flow in the other direction. In general, prosthetic heart valves include an orifice ring which forms the valve housing and which provides a central orifice or lumen for passage of blood. A valve mechanism, such as one or more occluders or leaflets, is mounted in the orifice and opens and closes to regulate the passage of blood. The housing and occluders collectively form the valve body. One such valve is disclosed in U.S. Pat. No. 4,276,658.

To attach the valve body to the tissue of the heart, typically a sewing cuff (also called a suture cuff) is provided. The sewing cuff for heart valve prostheses is generally a soft, flexible torus-like element through which sutures may pass to secure the sewing cuff, and consequently the heart valve, to the heart tissue.

One technique for attaching a sewing cuff to a valve body is illustrated in U.S. Pat. No. 4,276,658. In that embodiment, the valve body includes a groove that is used in coupling the sewing cuff to the valve body.

Another method of coupling the sewing cuff to the valve body is shown in U.S. Pat. No. 5,071,431 to Sauter et al. Sauter et al. discloses a heart valve where a sewing cuff is attached to a stiffening ring, with the stiffening ring being coupled to the valve body by a lock ring which rides in grooves in the outer periphery of the valve body and the inner periphery of the stiffening ring.

After a damaged or diseased natural valve structure is removed from the patient, the prosthesis is typically seated in the proper orientation and the sewing cuff is sewn to the peripheral heart tissue. Depending on the particular valve structure, care must be taken to ultimately orient the valve to ensure that the valving mechanism is in the most favorable anatomical position to provide proper blood flow and to ensure that the valve operates without interference from surrounding heart tissue. This must either be done before the sewing cuff of the valve is sutured into place, or if the sewing cuff is rotatable relative to the valve body (rotatable sewing cuff valve), this can be done after the sewing cuff is secured to the heart tissue. While this latter arrangement is convenient and can obviate the need to remove and resuture a valve to effect a rotation, a rotatable sewing cuff valve must meet several criteria.

For example, the torsional force required to rotate the valve body relative to the sutured cuff must be low enough so that the surgeon is able to rotationally position the valve with ease and without damage to the surrounding tissue. Once implanted, however, the valve body must maintain the desired position during the remainder of the surgery, and thereafter. Consequently, the torque required to initiate rotation must be great enough to prevent spontaneous rotation in vivo. Thus, the torsional force required to rotate the valve body within the sewing cuff should be predictable and fall within a narrow predetermined range such that the valve body may be easily rotated by the surgeon, yet is resistant to undesirable in vivo rotation once implanted.

The torsional force required to rotate the valve body relative to the sewing cuff will be determined by the manner in which the sewing cuff is retained on the valve body. Various methods have been proposed to rotatably secure the sewing cuffs of heart valve prostheses to the valve bodies. For example, U.S. Pat. No. 4,197,593 to Kaster et al. discloses a heart valve where a sewing cuff is sutured to a polymeric slip ring that slides along the surface of the valve body. U.S. Pat. No. 4,535,483 to Klawitter et al. discloses a heart valve where the sewing cuff is carried by deformable metal retainer rings that engage a stiffening ring disposed in and secured to a peripheral groove in the valve body. U.S. Pat. No. 5,104,406 to Curicio et al. discloses a heart valve where the fabric of the sewing cuff is stitched to a core, which directly abuts and rides the groove in the valve body. The core and the valve additionally sandwich the fabric along the annular space where the fabric is stitched to the core. U.S. Pat. No. 5,178,633 to Peters discloses a heart valve where the sewing cuff is coupled to the valve body by continuous fastener bands. The frictional engagement between the fabric tube and the valve body or "orifice ring" is controlled by the internal diameter of the fastener bands, which may be manufactured with precision. U.S. Pat. No. 5,876,463 to Vanney et al. discloses a rotatable heart valve which employs a spring for actively and independently exerting a controlled force directed substantially radially inward onto the outer circumference of the heart valve prosthesis.

Although several rotatable sewing cuff valves are available, these prior art devices typically suffer from one or more shortcomings. These shortcomings may include but are not limited to complexity of manufacture, undesirable variation in torque needed for rotation, excessive bulk, or insufficient radiopacity. Therefore, a need exists for an improved rotatable heart valve prosthesis. Moreover, the desired torque characteristics should be repeatable from valve to valve without surgically significant variation. Limitations of space within the implant site require that the cuff retention mechanism preferably be compact. Preferably, the retention mechanism should provide enhanced radiopacity to the valve.

SUMMARY OF THE INVENTION

A prosthetic heart valve is provided that includes an orifice ring adapted to carry blood therethrough. An annular recess is formed in an outer surface of the orifice ring and has first and second axially spaced walls. A sewing cuff is adapted to be coupled to a native tissue annulus of a heart and includes an inner annular cuff portion adapted to conform to the first and second recess walls in the orifice ring. A cuff retaining ring extends around the inner annular fabric portion such that the inner annular cuff portion is positioned between the cuff retaining ring and the annular recess. The cuff retaining ring is further adapted to exert a substantially axially directed force directed against the annular cuff portion and first and second axially spaced walls of the annular recess whereby a controllable torque to rotate the cuff relative to the orifice ring is developed substantially due to friction between the first and second recess walls cuff portion and the annular recess.

DETAILED DESCRIPTION OF THE PREFERRED EMBODIMENTS

Figure 1:
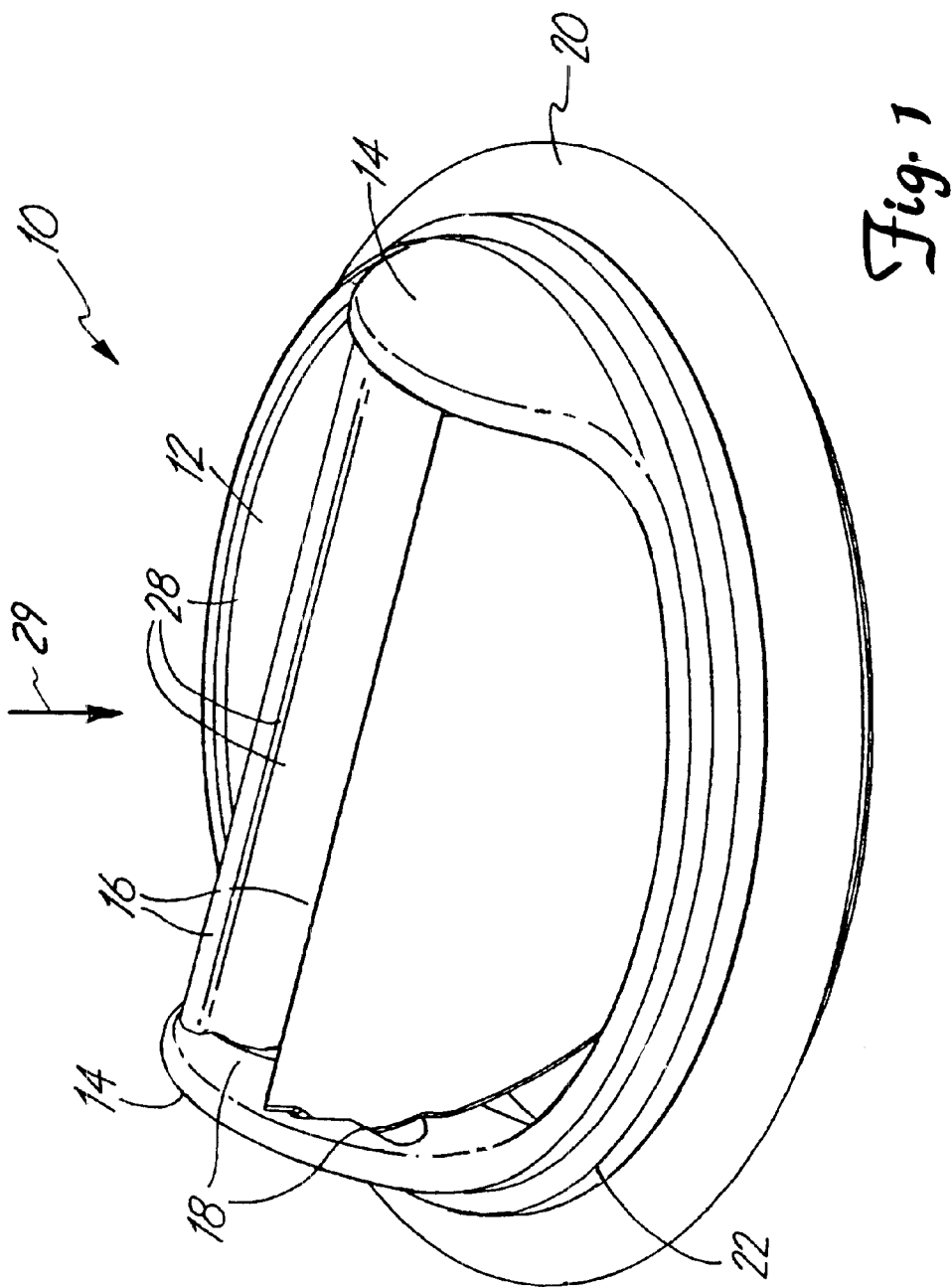
FIG. 1 is a perspective view of a prosthetic heart valve including a rotatable cuff in accordance with the present invention.

FIG. 1 is a perspective view of an assembled heart valve prosthesis 10 in accordance with the present invention. Prosthesis 10 includes orifice ring (or housing) 12 which carries pivot guards 14. Leaflets (occluder or occluders) 16 extend between pivot guards 14 and are pivotably carried in depressions 18 formed in pivot guards 14. The orifice housing 12 retains the leaflets 16 thus forming the valving mechanism also known as the valve body 28. In FIG. 1, leaflets 16 are shown in their open position.

However, leaflets can pivot to a closed position such that blood passage through orifice ring 12 is substantially blocked. In FIG. 1, valve 10 is positioned to allow blood flow in the direction indicated by arrow 29 and to block blood flow in the reverse direction.

A sewing cuff 20 extends around the outer diameter of orifice ring 12 and is secured in a recess 44 (not shown in FIG. 1) formed between distal rim 22 and proximal rim 42 (not shown in FIG. 1).

Prosthetic valve 10 is attached to the tissue annulus of a patient's heart after the natural tissue valve has been excised by a surgeon. Attachment of the valve 10 is through the use of sewing cuff 20. Sutures are run through sewing cuff 20 and the natural tissue annulus to secure valve 10 to the heart tissue. As will be described below in greater detail, after the sewing cuff 20 has been attached to the heart tissue, the orifice ring 12 can be rotated relative to cuff 20 to achieve a desired angular position of the valve body 28, including orifice ring 12 and leaflets 16 relative to the heart.

Figure 2:
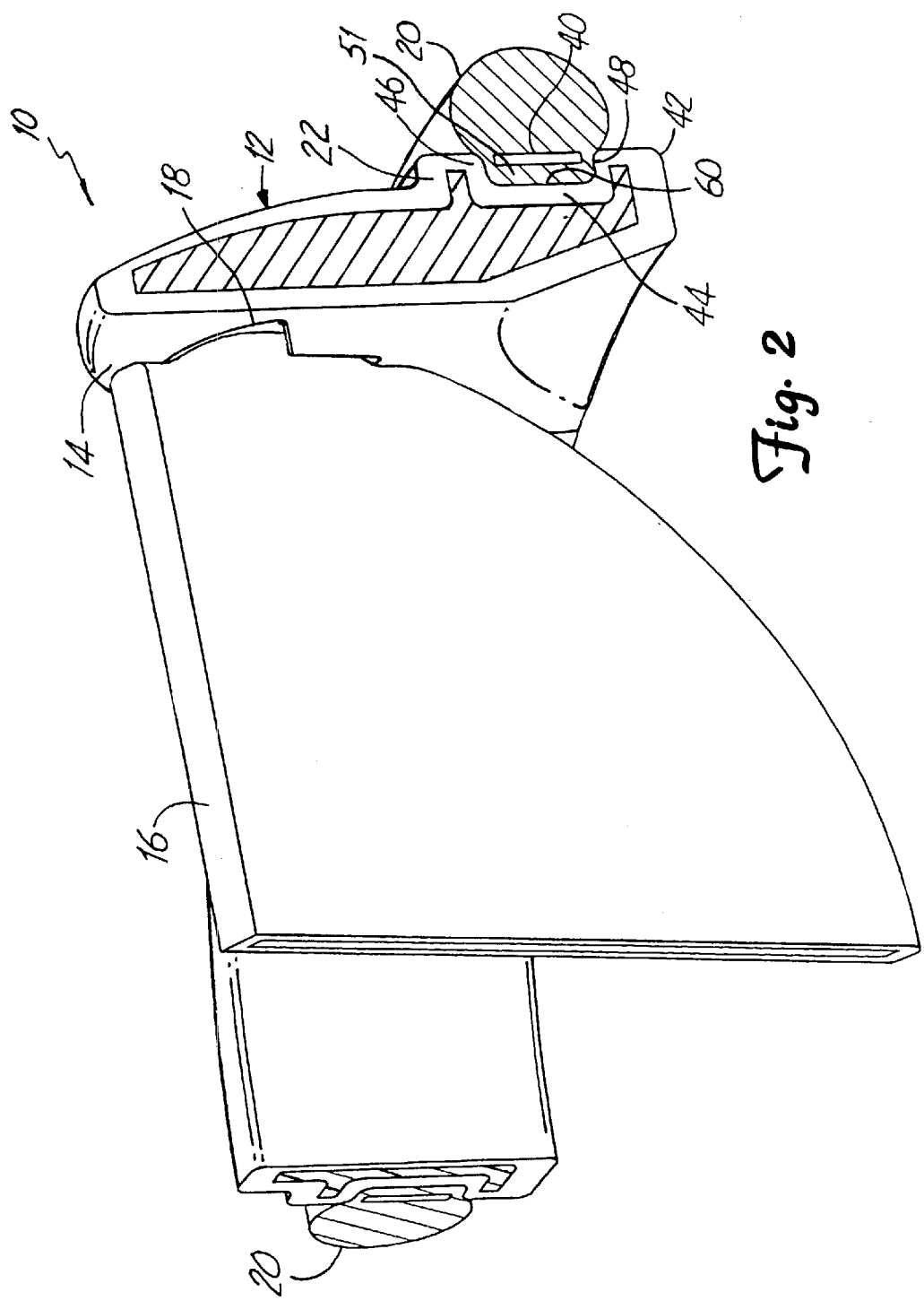
FIG. 2 is a sectional perspective view of a portion of the prosthetic heart valve of FIG. 1.

FIG. 2 is a sectional perspective view of heart valve prosthesis 10 which illustrates the attachment of cuff 20 to orifice ring 12 in greater detail. Cuff 20 includes a cuff retaining ring 40 and is positioned between distal rim 22 and proximal rim 42 in the recess 44 formed therebetween. Recess 44 is spaced between a first wall 46 and a second wall 48 which are axially spaced apart and formed by distal rim 22 and proximal rim 42, respectively. Recess 44 is bounded by annulus 60 formed by an outer circumference of orifice ring 12. As set forth in the description of FIG. 3, cuff retaining ring 40 has a width and length which place a substantially axially directed force against walls 46 and 48 to achieve a desired rotation torque. In the embodiment illustrated in FIG. 2, cuff retaining ring 40 is carried within sewing cuff 20 and any pressure or force from cuff retaining ring 40 against orifice ring 12 is transmitted through an inner annular portion 51 of the sewing cuff 20. FIG. 4 is a perspective view of cuff retaining ring 40 showing an inner annulus 62, an outer annulus 64, a distal edge 66 and a proximal edge 68.

Figure 3:
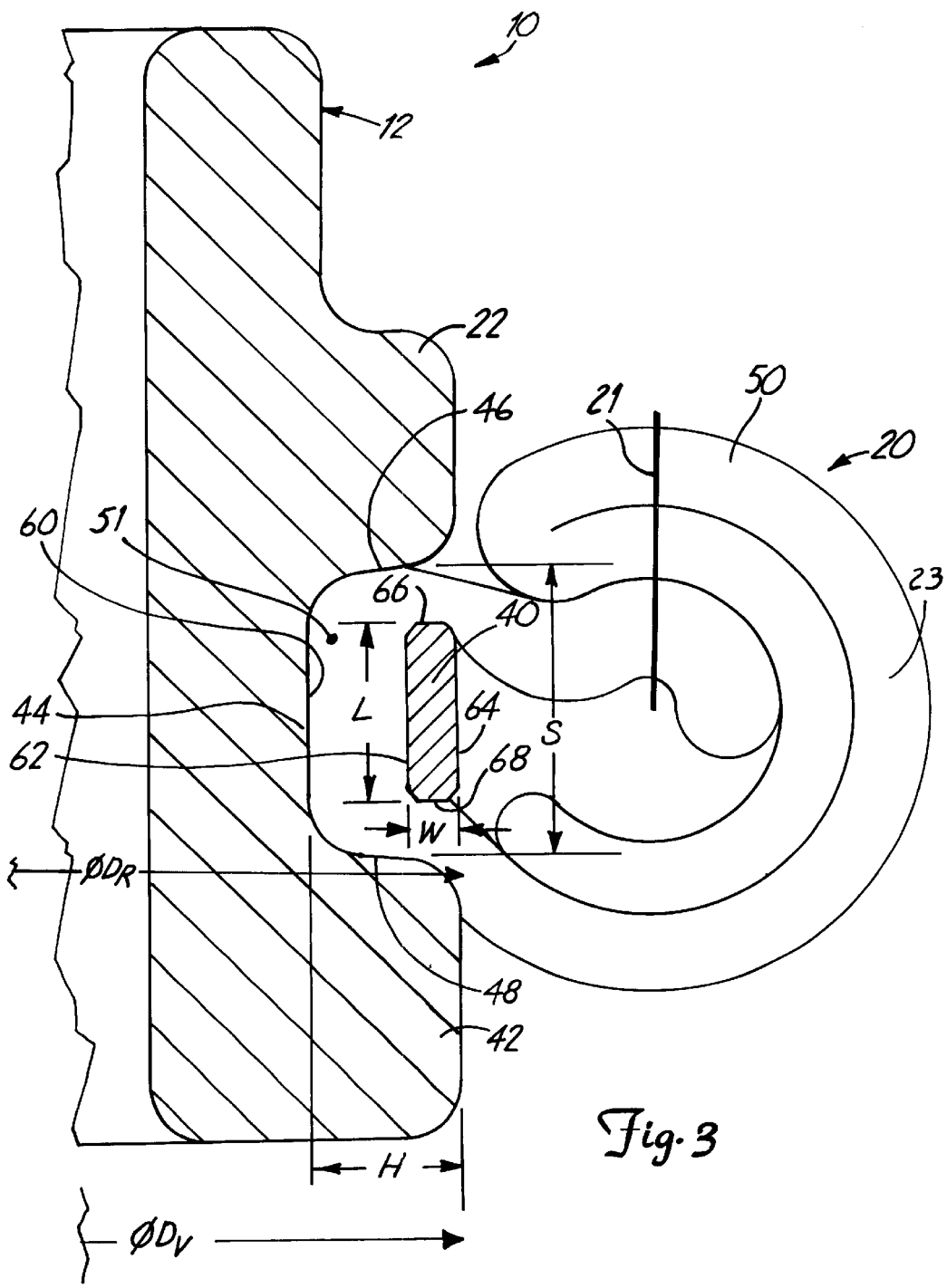
FIG. 3 is a cross-sectional view of a portion of the prosthetic heart valve of FIG. 1.
Figure 4:
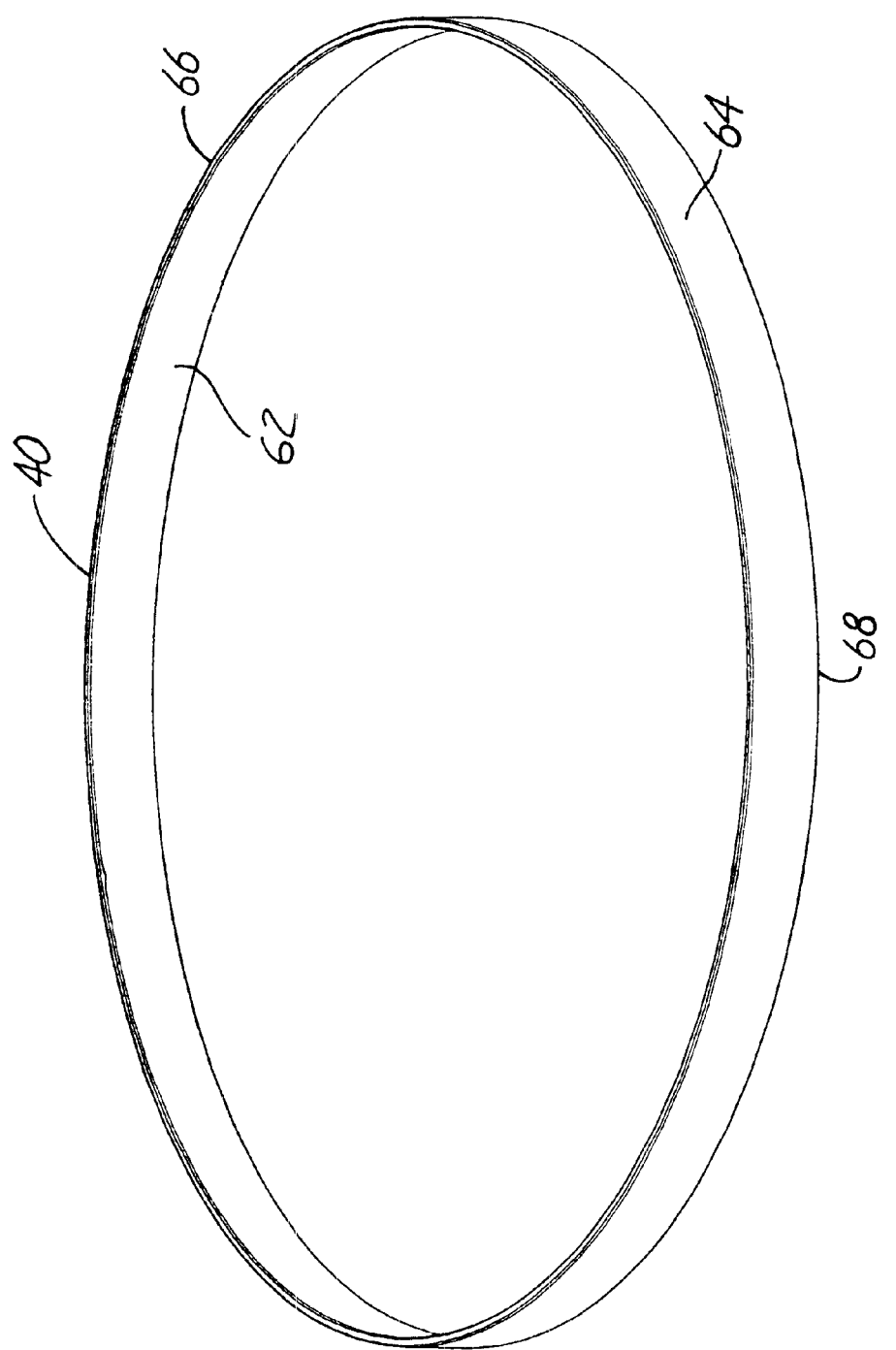
FIG. 4 is a perspective view of a cuff retaining ring that is a component of the prosthetic heart valve of FIG. 1.

FIG. 3 is a cross-sectional view of a portion of orifice ring 12 showing the attachment of cuff 20 to ring 12 in greater detail. As illustrated in FIG. 3, cuff retaining ring 40 is carried within folds of fabric tube 50 which form suture sewing cuff 20. In the particular embodiment shown, a single layer of fabric separates cuff retaining ring 40 from orifice ring 12. The sewing cuff is folded upon itself and secured or self-adhered with suture 21 to form exterior fold 23. A preferred material for cuff retention ring 40 is a cobalt-nickel-chromium-molybdenum alloy known as MP-35N, but other high strength biocompatible metals including alloys of cobalt or of titanium may be used. Fabric tube 50 is preferably made from a biocompatible material such as polyester fabric. However, any biocompatible material that can be readily compressed and that provides a moderate back force when somewhat compressed, such as elastomers including silicones and polyurethanes and fabrics including those made with polyterefluoroethylene (PTFE) may be used to form fabric tube 50. The sewing cuff preferably is composed of at least an outer layer of fabric since fabric typically provides good tissue ingrowth. The material of fabric tube 50 is preferably biocompatible and should also be somewhat pliable. Preferably, the fabric of fabric tube 50 is organized into a structure which is most preferably knitted, but in other embodiments, the fabric tube 50 may be a woven or non-woven structure.

FIG. 3 also shows radial width W and axial length L of cuff retaining ring 40, the axial spacing S between walls 46 and 48 and the radial depth or height H of recess 44 relative to the circumference of distal rim 22 and proximal rim 42. To achieve a desired torque and retention of cuff 20 in recess 44, the length L of cuff retaining ring 40 is selected to provide a relatively small clearance relative to S, the spacing between walls 46 and 48. This significantly compresses an inner portion 51 of fabric tube 50 against walls 46 and 48. This compression causes cuff retaining ring 40 to apply a substantially axially directed force against walls 46 and 48 which largely determines the torque required to rotate orifice ring 12 relative to cuff 20.

Further, cuff retaining ring 40 is configured to provide a relatively large clearance with respect to the inner annulus ring 62 and recess 44. Specifically, the difference between the height H and the width W is such that there is little or no compression of fabric tube 50 in the radial direction against annulus 60 This combination of clearances, with S minus L smaller than H minus W, provides a very consistent torque required to rotate sewing cuff 20 relative to orifice ring 12 while also securely attaching cuff 20 to ring 12. The portion of fabric tube 50 which fits within recess 44 provides an inner annular cuff portion 51.

In a preferred embodiment, the outer diameter $D_R$ of the cuff retaining ring is less than or equal to the maximum outer diameter $D_V$ of each of the proximal rim 42 and distal rim 22, to minimize bulk which may interfere with patient's tissue or with surgeon's suture needle.

Figure 5:
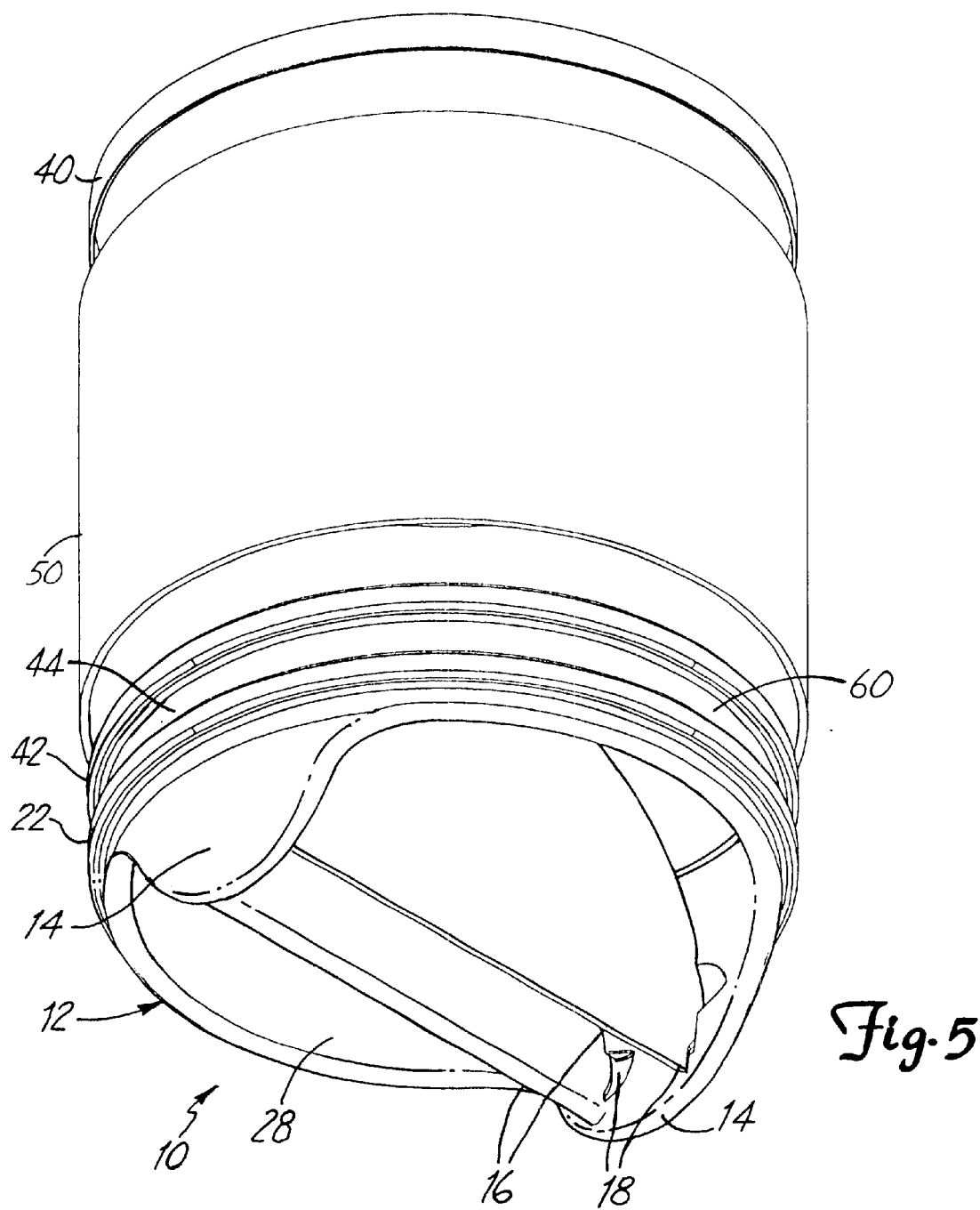
FIG. 5 is an exploded perspective view showing steps of assembling an orifice ring of a valve body with a fabric tube and a cuff retention ring in accordance with the present invention.
Figure 6:
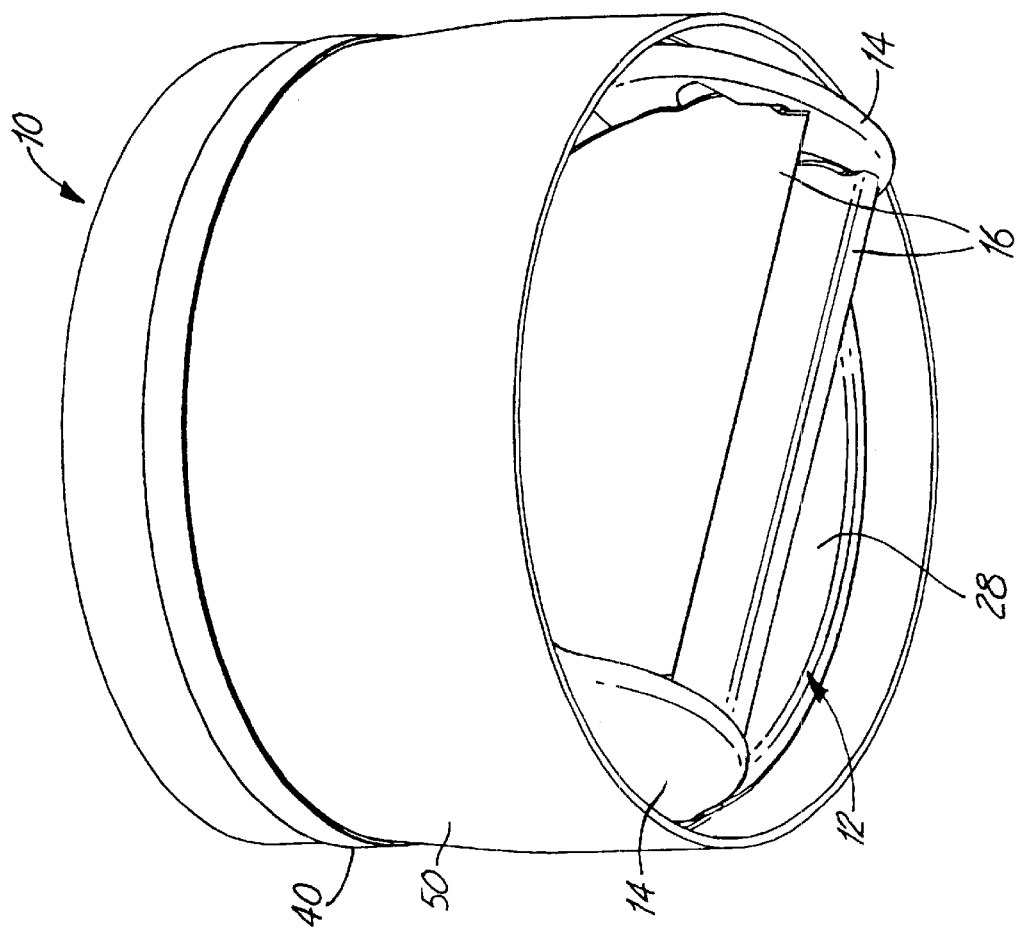
FIG. 6 is a perspective view showing another step in the assembly in which the cuff retention ring and the fabric tube have been placed adjacent to and over the orifice ring, respectively.

FIGS. 5–9 are perspective views showing the steps of assembling sewing cuff 20 onto orifice ring 12 of prosthetic valve 10. FIG. 5 shows an exploded view of valve body 28, which includes orifice ring 12, fabric tube 50, and cuff retaining ring 40. In FIG. 6, valve body 28 including orifice ring 12 is supported in an assembly apparatus 100 (not shown in FIG. 6, see FIG. 10) and has been placed inside of fabric tube 50. Cuff retaining ring 40 is placed around fabric tube 50. Preferably, leaflets 16 are inserted into orifice ring 12 forming valve body 28 prior to attachment of cuff 20 because the presence of the cuff retaining ring 40 may interfere with the process of inserting the leaflets 16. Preferably, valve body 28 is placed into the valve assembly apparatus 100 with pivot guards 14 facing down to allow assembly of the fabric tube 50 and cuff retaining ring 40 over the proximal rim 42.

Figure 7:
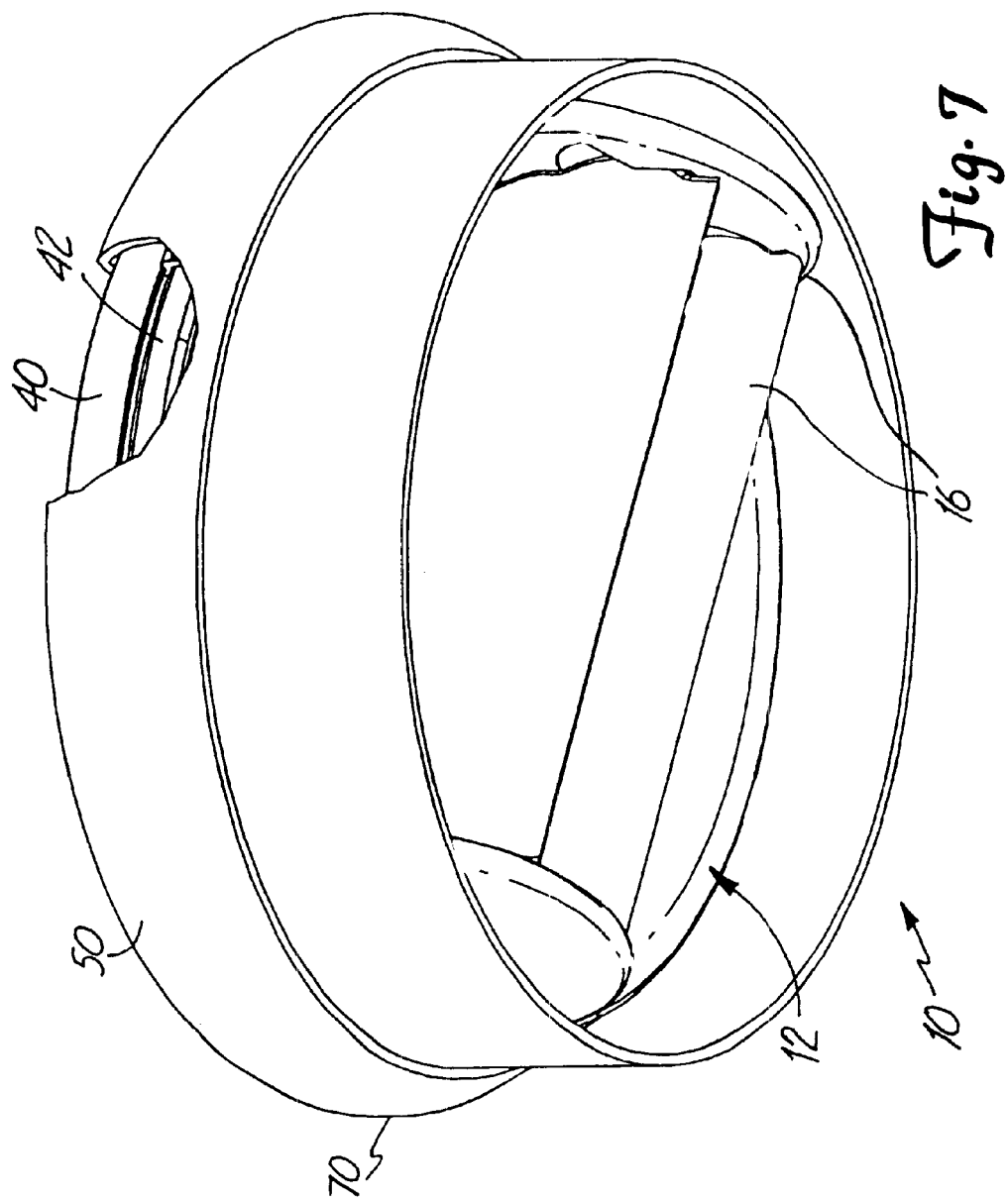
FIG. 7 is a perspective cut away view of another step in the assembly in which the fabric has been folded over the retention ring.
Figure 8:
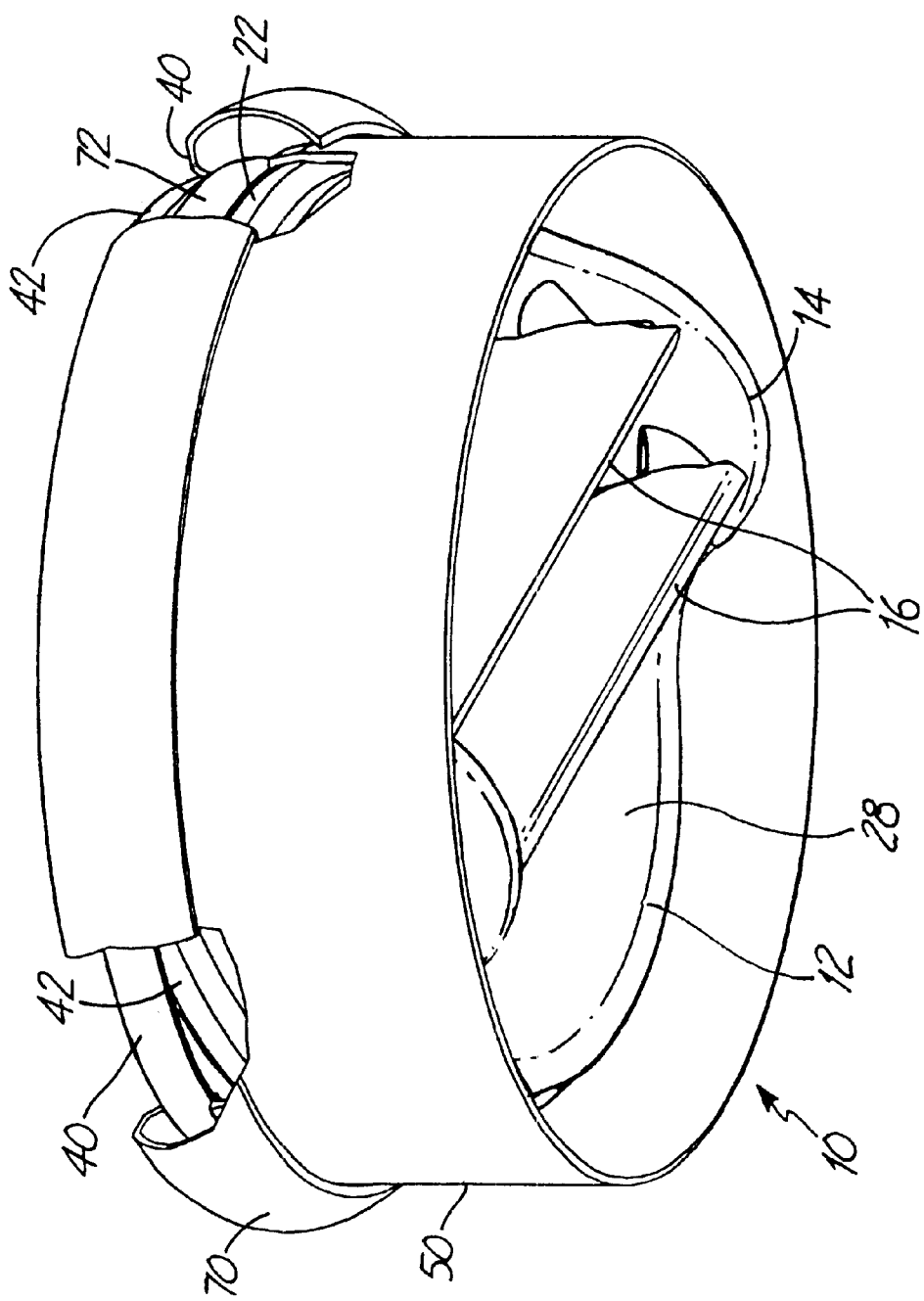
FIG. 8 is a perspective cut away view of the assembly process in which the fabric and the cuff retention ring have been placed in an intermediate position.
Figure 10:
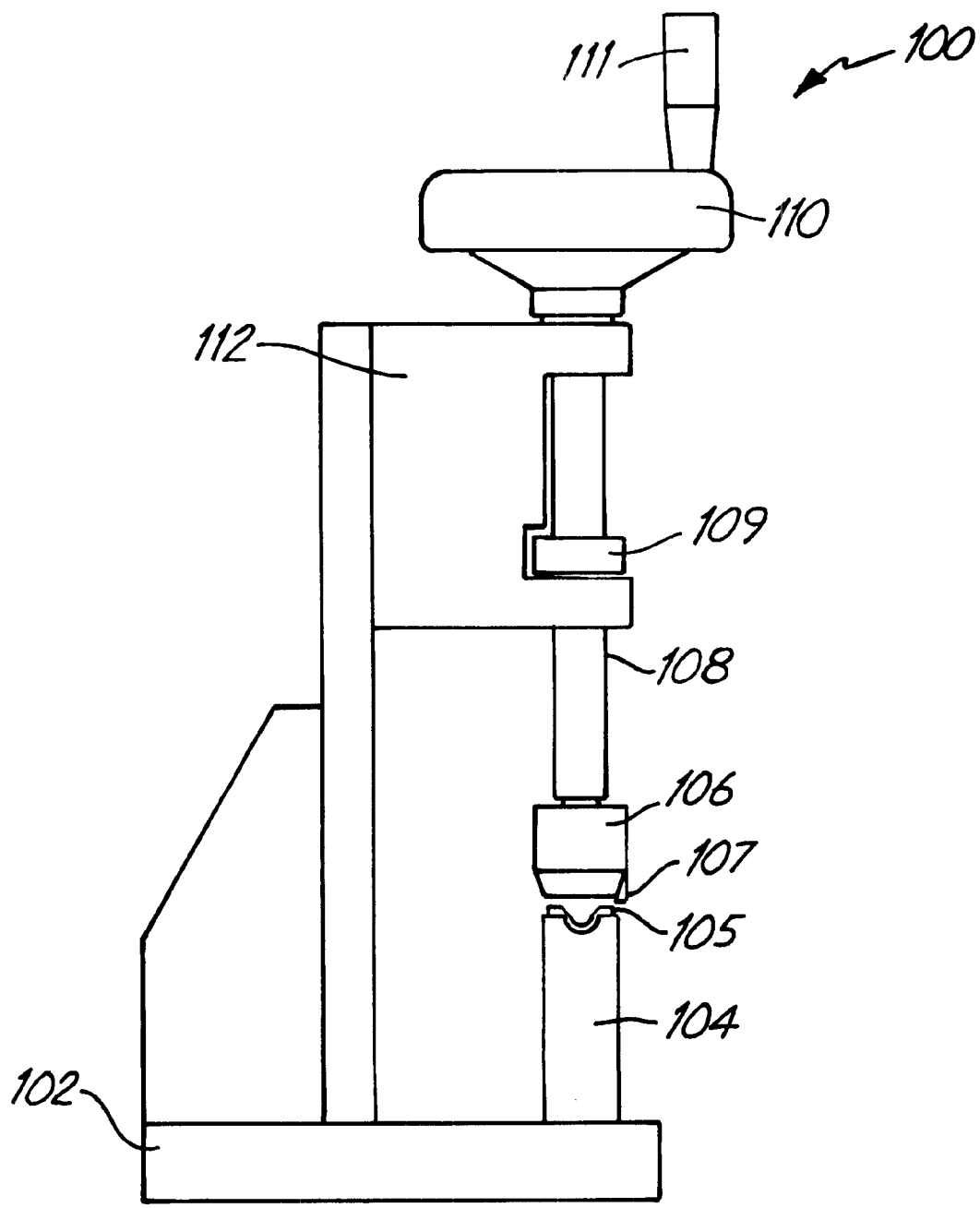
FIG. 10 is a plan view of an apparatus used in the assembly of the sewing cuff to the valve body to form prosthetic heart valve of FIG. 1 and used in the steps illustrated in FIGS. 5–9.

In FIG. 7, fabric tube 50 is shown with fold 70 which extends around cuff retaining ring 40. Ring 40 is positioned adjacent proximal rim 42. In FIG. 8, cuff retaining ring 40 and fold 70 are shown in an intermediate position achieved by operation of assembly apparatus 100 (FIG. 10). In the intermediate position, one side 72 of cuff retaining ring 40 is positioned in recess 44. The other side of cuff retaining ring 40 which is 180° from side 72 has not yet been placed into recess 44 and is pressed against proximal rim 42. The movement of cuff retaining ring 40 is made possible due to the compressibility of the fabric of fabric tube 50 and the elasticity of the ring 40 and orifice ring 12. To prevent undesirable distortion or fracture of cuff retaining ring 40 during the assembly process, several factors must be considered. The ring 40 must be of a biocompatible material which is relatively strong and the inside diameter and thickness of ring 40 must be carefully matched to the diameter of proximal rim 42.

Figure 9:
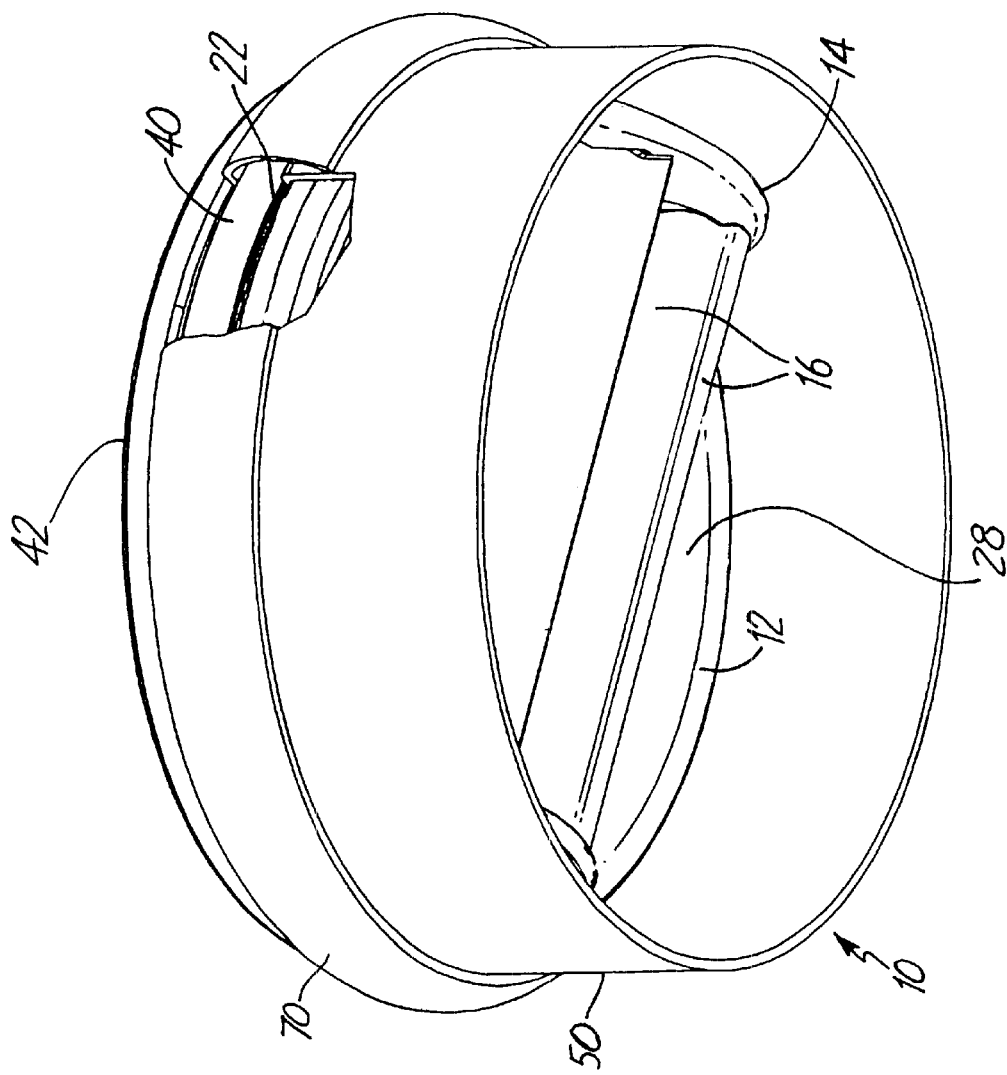
FIG. 9 is a cut away perspective view showing a step in the assembly process in which the retention ring has been moved into a final position.

In FIG. 9, cuff retaining ring 40 is shown completely seated within recess 44 achieved by operation of assembly apparatus 100 shown in FIG. 10. Next, fabric tube 50 is folded exterior to the valve body 28 and retention ring 40 and adhered to itself, preferably with sutures 21 (not shown in FIG. 9) to form a sewing cuff 20 as illustrated in FIG. 3. While the preferred self-attachment method uses sutures, other self-attachment methods include use of chemical adhesive and metal staples. In a preferred embodiment, the cuff 20 includes only the fabric of fabric tube 50. In one embodiment, a biocompatible filler material, such as a silicone ring, is included in the exterior fold 23 of sewing cuff 20.

FIG. 10 is a side plan view of a cuff assembly apparatus 100 for use in assembling a prosthetic heart valve body and sewing cuff in accordance with the present invention. Assembly apparatus 100 includes base 102 and orifice ring support 104 which carries orifice ring 12 (not shown in FIG. 10) by means of mating feature 105. Mating feature 105 captures pivot guards 14 and prevents rotation of the valve body relative to the orifice ring support 104. A cuff insertion finger 107 is fixed to and projects downward from a cuff insertion head 106 and is adapted to press upon the fabric tube 50 and cuff retaining ring 40 during the assemble process with respect to FIGS. 5–9. Head 106 is coupled to wheel 110 and handle 111 through shaft 108, which is rotatably carried in support 112. During assembly, fabric tube 50 is placed over orifice ring 12. Then cuff retaining ring 40 is placed over fabric tube 50 and above proximal rim 42. A fold 70 of fabric tube 50 is then brought over retaining ring 40. Wheel 110 is then rotated while head 106 moves downward, limited by stop 109, to engage finger 107 with the cuff retaining ring 40 which is covered by fold 70. The force conveyed through finger 107 thereby momentarily stretches a subjacent portion of cuff retaining ring 40 while momentarily compressing a corresponding volume of fabric tube 50. Thus, the subjacent portion of ring 40 is moved over proximal rim 42 and into recess 44. As the head 106 is rotated, the finger 107 pushes an increasing portion of retaining ring 40 into recess 44, until the entire cuff retaining ring 40 resides in recess 44 over the inner annular cuff portion of fabric tube 50 when finger 107 has sufficiently traversed around orifice ring 12. Other devices can be used to assemble the valve and device 100 is provided as one example.

In an embodiment, the annular cuff portion of fabric tube 50 is heated to above a glass transition temperature of its fabric under a compressive load prior to assembly. This results in a reduction in thickness in the annular cuff portion to a generally uniform value, which is beneficial in maintaining a consistent range of torque. In an embodiment, the material of fabric tube 50 includes a coating or impregnation such as an ion-beam implantation of a substance, for example, silver, toxic to bacteria or other microbes.

A heart valve prosthesis in accordance with the present invention provides a substantially controllable and predictable level of rotation resistance torque over a desired range. In one embodiment the torque required to rotate the cuff relative to the orifice ring is between about one and about fifteen ounces-inches. Further, such prosthesis requires only a single cuff retention ring which can be manufactured to be relatively thin to thereby reduce the bulk of stiff cuff retention mechanism. Indeed, for a preferred embodiment, the cuff retention ring does not extend past the outermost surface of the valve housing. This prevents interference with patient's tissues and provides a maximum volume of sewing cuff available for suturing. Thus, minimizes the chance of the ring impeding suture needle penetration. Furthermore, the thin cross-sections of the valve housing and cuff retention ring over-all allows an increase in the lumen area of the prosthesis, thereby improving blood flow. This improvement in blood flow is highly beneficial to the patient.

The rotation mechanism of the invention provides a relatively low profile (i.e., thin in an axial direction) design in comparison to prior art configurations. The present rotation mechanism requires only a relatively small area. Further, the mechanism is relatively thin in a radial direction. Preferably, the ring 40 does not extend in a radial direction beyond the outer radius of rings 22 and 42 such that a large amount of cuff 20 is available for suturing.

Other benefits of the present invention include the following. The metal cuff retaining ring provides radiopacity. The components can be manufactured using standard prosthetic valve manufacturing techniques. The assembly steps do not require any critical adjustments by an operator to achieve a desired resistance to rotation.

Although the present invention has been described with reference to preferred embodiments, workers skilled in the art will recognize that changes may be made in form and detail without departing from the spirit and scope of the invention.

What is claimed is:

1. A prosthetic heart valve, comprising:
   a valve body consisting of an orifice ring and an occluder;
   the orifice ring adapted to carry blood therethrough when an occluder is in its open position;
   an annular recess formed in an outer surface of the orifice ring which defines first and second axially spaced walls in the outer surface of the orifice ring;

a compressible sewing cuff adapted to be coupled to a native tissue annulus of a heart, the cuff including an inner annular cuff portion adapted to conform to the first and second recess walls in the orifice ring; and a stiff cuff retaining ring adapted to extend around the inner annular cuff portion such that the inner annular cuff portion is positioned between the cuff retaining ring and the annular recess, the cuff retaining ring further adapted to exert a substantially axial force directed in an axial direction through the cuff and against the first and second axially spaced walls of the annular recess, said axial force being substantially greater than a radial force directed substantially inwardly by the cuff retaining ring against an annulus of the recess located between the first and second walls, whereby a controllable torque to rotate the sewing cuff relative to the valve body is developed substantially due to friction between the first and second recess walls and the inner annular cuff portion.

2. The prosthetic heart valve of claim 1 wherein the sewing cuff retaining ring comprises a biocompatible high-strength metal.

3. The prosthetic heart valve of claim 2 wherein the metal of the cuff retaining ring consists of an alloy of cobalt.

4. The prosthetic heart valve of claim 3 wherein the ring provides radiopacity to the heart valve.

5. The prosthetic heart valve of claim 2 wherein the metal of the cuff retaining ring includes titanium and alloys thereof.

6. The prosthetic heart valve of claim 1 wherein the sewing cuff comprises a biocompatible, pliable and compressible fabric structure.

7. The prosthetic heart valve of claim 1 wherein the sewing cuff comprises fabric and the cuff retaining ring is carried within the cuff.

8. The prosthetic heart valve of claim 1 wherein the sewing cuff is adapted to receive a suture therethrough to affix the cuff to the tissue annulus.

9. The prosthetic heart valve of claim 1 wherein an outer diameter of the cuff retention ring does not exceed a maximum outer diameter of the valve body.

10. The prosthetic heart valve of claim 1 wherein the torque required to rotate the cuff relative to the orifice ring is between about 1 and about 15 oz-inches.

11. The prosthetic heart valve of claim 1 including first and second rims in the orifice ring to provide the first and second axially spaced walls and define the annular recess therebetween.

12. The prosthetic heart valve of claim 1 wherein an axial distance(s) between the first and second axially spaced walls minus an axial length (L) of the cuff retaining ring is less than or equal to a height (H) of the recess minus a width (W) of the cuff retaining ring.

13. The prosthetic heart valve of claim 1 wherein the prosthetic heart valve provides a relatively low profile.

14. A method of manufacturing a heart valve prosthesis, comprising:

folding a tube of biocompatible, pliable, compressible material over a stiff cuff retaining ring;

positioning a portion of the cuff retaining ring and tube material in an annular recess of an orifice ring, the annular recess formed between first and second axially spaced walls;

positioning a remainder of the cuff retaining ring into the annular recess, wherein the cuff retaining ring substantially compresses the material against the first and second axially spaced walls and substantially does not compress the tube material radially against the annulus of the recess such that an axial force against the first and second walls of the recess is substantially greater than a radial force directed substantially inwardly by the cuff retaining ring against an annulus of the recess located between the first and second walls; and affixing the tube material to itself to form a sewing cuff.

15. The method of claim 14 wherein the tube material is affixed to itself using sutures to form a sewing cuff.

16. The method of claim 14 wherein a portion of the tube of biocompatible, pliable, compressible material is reduced in thickness prior to assembly.

17. The method of claim 14 wherein an axial distance(s) between the first and second axially spaced walls minus an axial length (L) of the cuff retaining ring is less than or equal to a height (H) of the recess minus a width (W) of the cuff retaining ring.

* * * * *